(12) United States Patent
Rockseisen

(10) Patent No.: US 7,594,752 B2
(45) Date of Patent: Sep. 29, 2009

(54) APPARATUS AND METHOD FOR CHECKING THE ALIGNMENT OF LASER BEAMS ON A DIAGNOSTIC AND/OR THERAPEUTIC MACHINE

(75) Inventor: Armin Rockseisen, Scharnebeck (DE)

(73) Assignee: LAP GmbH Laser Applikationen, Luneburg (DE)

( * ) Notice: Subject to any disclaimer, the term of this patent is extended or adjusted under 35 U.S.C. 154(b) by 309 days.

(21) Appl. No.: 11/742,913

(22) Filed: May 1, 2007

(65) Prior Publication Data
US 2007/0284543 A1    Dec. 13, 2007

(51) Int. Cl.
A61B 6/08 (2006.01)
(52) U.S. Cl. .............................. 378/205; 378/19; 378/62
(58) Field of Classification Search .............. 250/491.1, 250/492.3; 378/205, 209, 196
See application file for complete search history.

(56) References Cited

U.S. PATENT DOCUMENTS

| | | | | |
|---|---|---|---|---|
| 4,481,656 | A * | 11/1984 | Janssen et al. | ............... 378/196 |
| 4,589,126 | A * | 5/1986 | Augustsson et al. | ......... 378/209 |
| 5,142,559 | A * | 8/1992 | Wielopolski et al. | ........ 378/205 |
| 6,670,618 | B1 * | 12/2003 | Hartmann et al. | ........ 250/491.1 |
| 6,745,072 | B1 * | 6/2004 | Badura et al. | ................... 607/2 |
| 6,799,068 | B1 * | 9/2004 | Hartmann et al. | ............... 607/2 |
| 6,806,712 | B2 * | 10/2004 | Akgun | ........................ 324/318 |
| 6,865,253 | B2 * | 3/2005 | Blumhofer et al. | ............ 378/65 |
| 2002/0085668 | A1 * | 7/2002 | Blumhofer et al. | ............ 378/68 |
| 2006/0064008 | A1 * | 3/2006 | Moore | ......................... 600/425 |
| 2009/0052760 | A1 * | 2/2009 | Smith et al. | .................. 382/132 |

FOREIGN PATENT DOCUMENTS

| | | |
|---|---|---|
| DE | 197 50 004 A1 | 6/1999 |
| DE | 199 07 065 A1 | 8/2000 |
| EP | 0 753 285 A1 | 4/1996 |
| GB | 2 317 545 A | 8/1996 |
| WO | 02/100477 A2 | 12/2002 |
| WO | 2006/05570 A2 | 5/2006 |

* cited by examiner

*Primary Examiner*—Nikita Wells
*Assistant Examiner*—Johnnie L Smith
(74) *Attorney, Agent, or Firm*—Vidas, Arrett & Steinkraus, P.A.

(57) ABSTRACT

An apparatus for checking the alignment of laser beams for indicating a position in relation to a diagnostic and/or therapeutic machine, which has a isocentre, wherein the machine has a patient support movable in its position, laser beams and isocentre being aligned in relation to each other such that the laser beams intersect with each other in the isocentre of the machine, wherein the machine has the following a carrier element, which is provided with means for being arranged in a predetermined position on the patient support of the machine, a first and a second measuring device, each one at a time being equipped with connection means for the carrier element, wherein the first measuring device measures the position of the impingent laser beams with respect to a predetermined position in relation to the patient support, the second measuring device records the position of the isocentre in relation to the predetermined position of the first measuring device.

13 Claims, 2 Drawing Sheets

APPARATUS AND METHOD FOR CHECKING THE ALIGNMENT OF LASER BEAMS ON A DIAGNOSTIC AND/OR THERAPEUTIC MACHINE

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention is related to an apparatus and a method for checking the alignment of laser beams on a diagnostic and/or therapeutic machine, the laser beams having the purpose to indicate a treatment position in relation to a therapeutic beam.

In radiation therapy, different diagnostic imaging methods are used in order to examine a patient in more detail. In particular, imaging methods are applied when there is a suspicion of a tumour disease, in order to represent location, size and position of the tumour in the patient's body in an image. For later irradiation of the tumour, a therapeutic device is used at a later point of time, which makes transfer of the diagnostic results to the therapeutic device necessary. When the location of the tumour is determined in the imaging process, it is necessary that at a later point in time, the patient should be aligned in relation to the therapeutic machine such that the therapeutic beam runs through the tumour. With a movable therapeutic beam, which impinges from different directions onto the region to be treated, it has to be taken care for the correct alignment of the patient that the isocentre of the therapeutic beam is located in the predetermined position. In a diagnostic machine, there is no machine-determined isocentre, but another mechanical reference point depending on the type of the machine, a so-called virtual isocentre. In a computer tomograph for instance, the virtual isocentre is defined on the rotational axis. In the following text, it is not distinguished between the isocentre of the therapeutic machine and the virtual isocentre of the diagnostic machine.

In order to bring the patient on the machine into a predetermined position, so that the tissue region to be treated is aligned accurately in relation to the therapeutic beam, markers are applied on the patient's skin in the diagnostic procedure. The locations for the markers are projected onto the patient's skin by lasers on the machine which executes the diagnostic procedure, for instance. The markers can be transferred to the patient's skin with a pencil, for instance. Also, it is possible to stick markers on the skin. For instance, the laser beams can be directed to a point which is envisioned as the future isocentre. When the patient is on the therapeutic machine, some days later, for instance, he/she is aligned by means of the markers on the therapeutic machine into a position allowing a determination of the treatment region. In order to perform accurate alignment of the patient, laser beams are projected onto the patient's skin again in an accurately defined way on the therapeutic machine, too. When the applied markers are coincident with the laser beams projected onto the skin, the patient is in the defined position again, so that size, location and alignment of the tissue region to be treated is accurately accomplished for the control of the therapeutic machine by means of the diagnostic data. When aligning the patient, the patient can be aligned again to the isocentre of the therapeutic beam on the therapeutic machine too, when the laser beams on the diagnostic machine are directed towards the envisioned isocentre.

The present invention is based on the objective to check on a therapeutic machine whether the laser beams for marking are correctly aligned in relation to the therapeutic beam.

BRIEF DESCRIPTION OF THE INVENTION

The apparatus according to the present invention serves for checking the alignment of laser beams for indicating a treatment position in relation to a therapeutic beam on a diagnostic and/or therapeutic machine. The machine has a movable patient support, the position of which is adjustable in relation to the therapeutic beam. For correct positioning of the patient in relation to the therapeutic beam, the laser beams and the therapeutic beam are aligned in relation to each other such that the laser beams intersect each other in an isocentre of the therapeutic beam. In a diagnostic machine, the laser beams intersect each other also in the isocentre. The apparatus according to the present invention has three components. A carrier element is provided for being arranged in a predetermined position on the patient support of the machine. For this purpose, the carrier element is provided with means which permit reproducible and defined positioning on the patient support of the machine. Further, a first and a second measuring device are provided, which are each one at a time equipped with connection means for the carrier element. Of the measuring devices, a first measuring device measures the position of the impingent laser beams in relation to a predetermined position with respect to the patient support. The second measuring device records the position of the isocentre in relation to the position of the first measuring device. Thus, with the apparatus according to the invention, there is the possibility to define a point in space by the predetermined position of the first measuring device, at which the alignment of the laser beams is compared and at which the alignment of the therapeutic beam or of a diagnostic unit of the diagnostic machine can take place. The apparatus according to the present invention provides an accurate tool for making the correct alignment of laser beams and therapeutic beam in relation to each other possible. In particular, a fine adjustment can be achieved in this way, which is not possible with a purely optical examination through guessing by eye.

In one preferred embodiment, the first measuring device has line sensors, which acquire the position of the laser beams on the measuring device. For the laser beams, line lasers are preferably used for the generation of markers, the line sensors being each at a time aligned transversely to the orientation of the light plane formed by the line laser in doing so. Preferably, the line sensors are aligned orthogonally to the light plane formed by the line laser.

Preferably, the first measuring device has at least three line sensors, which are oriented by pairs in different directions in the space. The alignment of the line sensors in three space directions permits a three-dimensional setting of the predetermined point on the basis of the laser beams impinging on the line sensors.

Advantageously, the line sensors of the first measuring device are connected to an analysing unit, which determines whether the laser beams intersect with each other in the predetermined position in relation to the patient support.

In a preferred embodiment, the analysing unit is realised to indicate for adjusting the lasers into a predetermined position which laser device deviates into which direction from the correct position. In a further development, the lasers are equipped with means for moving the position of the lasers, the analysing unit forwarding control signals for automatic alignment of the lasers into the desired position to the moving means.

In an advantageous embodiment, the second measuring device is provided with a sample body and a holder for a recording material. The recording material records an image of the sample body in the therapeutic beam. Recording material and sample body are arranged in the second measuring device in order to let the therapeutic beam project an image of the sample body onto the recording material. In a diagnostic machine, a recording material is used, for which the diagnostic beam generates an image of the sample body. In addition, an image of the isocentre is recorded in the therapeutic machine and the diagnostic machine, so that the deviation between sample body and isocentre is fixed on the recording material.

Advantageously, the sample body is arranged in the second measuring device in that position which describes the alignment of the lasers with respect to the first measuring device.

Preferably, with the predetermined position it is dealt with that position which the first measuring device compares with the alignment of the lasers and in which the sample body of the second measuring device is located, thus, with the expected isocentre of the machine. The expected isocentre of the machine, also designated as the desired position for the isocentre, is that point in space which the control unit of the machine presumes as the isocentre of the therapeutic beam. This point does not have to coincide with the real isocentre of the therapeutic beam or with the point which the control unit presumes as the reference point. Instead, the analysis of the second measuring device may have the result that expected isocentre and real isocentre do not coincide. In this case, the alignment of the therapeutic beam and/or the desired value for the isocentre in the control unit must be changed.

The objective according to the present invention is also resolved by a method for the alignment of laser beams for indicating a patient's position in relation to a machine. In this, the alignment of the laser beams in relation to a therapeutic beam comprises the possibility to align the laser beam and to let the therapeutic beam unchanged, as well as the possibility to let the laser beam unchanged and to align the therapeutic beam. Also, both beams can be changed in their spatial direction for alignment, in order to bring them into a correct position in relation to each other. In the method according to the present invention, a patient support is set into a predefined reference position. A carrier element is arranged in a defined position on the patient support. Using a first measuring device, a point of intersection of the laser beams is brought into coincidence with a predetermined position in relation to the patient support. Using a second measuring device, the isocentre of the therapeutic beam is brought into coincidence with the predetermined position in relation to the patient support. The first as well as the second measuring device are arranged on a carrier element in doing so, and the position of the patient supports in space or that of the carrier element in relation to the patient support remain unchanged between the usages of the measuring devices. The method according to the present invention is a process in two steps, in which the alignment of marking lasers and therapeutic beam are checked for a point fixed in space.

In one possible embodiment of the method according to the present invention, the usage of the second measuring device takes place at first, and subsequently alignment of the lasers using the first measuring device. Alternatively to this, it is also possible to use the first measuring device at first and subsequently to align the therapeutic beam using the second measuring device. This is particularly preferred when using particle beams for therapy, like proton beams for instance.

BRIEF DESCRIPTION OF SEVERAL VIEWS OF THE DRAWINGS

In the following, the present invention is explained in more detail by means of an example of its realisation.

DETAILED DESCRIPTION OF THE INVENTION

Figure 1:
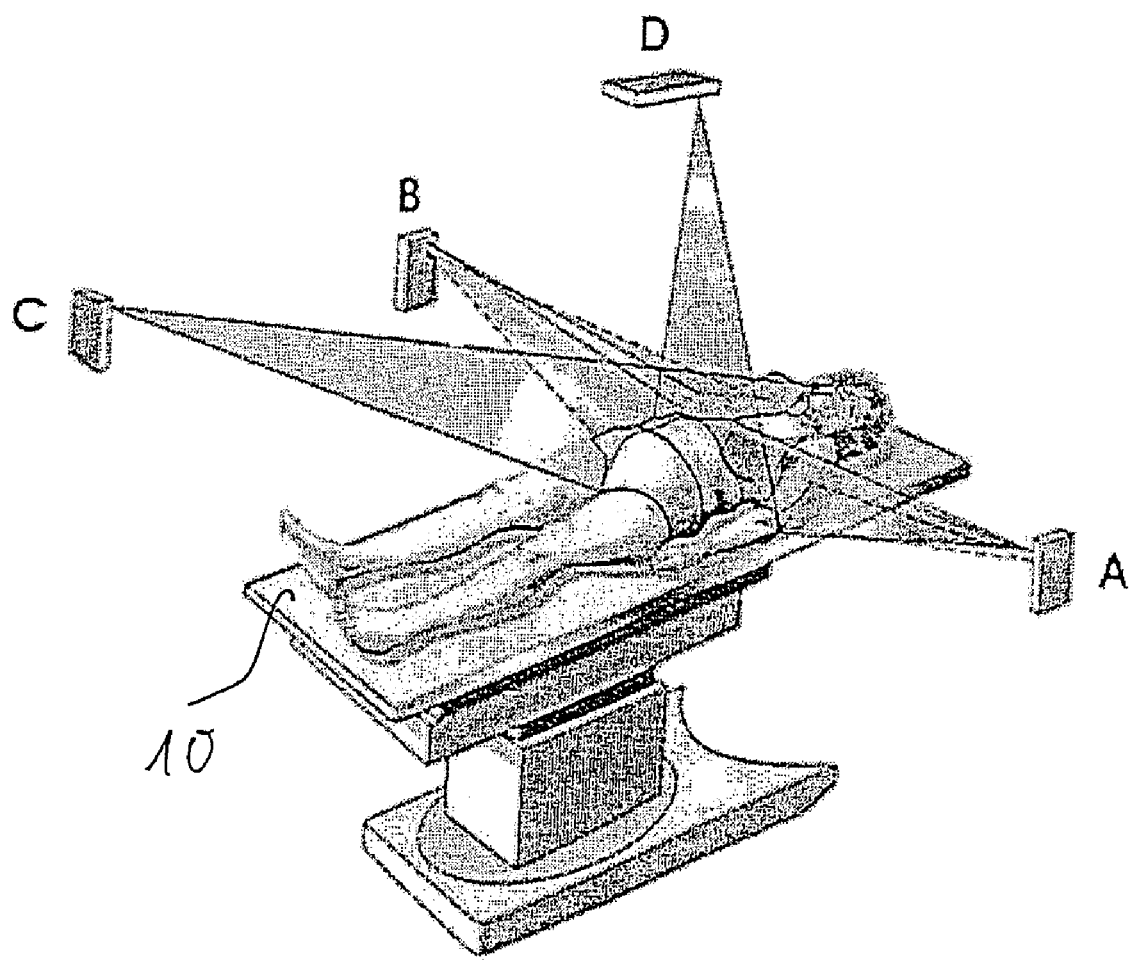
FIG. 1 shows a patient on a movable patient support, who is laid down on a treatment table.

While this invention may be embodied in many different forms, there are described in detail herein a specific preferred embodiment of the invention. This description is an exemplification of the principles of the invention and is not intended to limit the invention to the particular embodiment illustrated FIG. 1 shows a patient support 10 movable in its position, as it is installed in front of an irradiation apparatus. Via the four line lasers A, B, C, D, a coordinate system fixedly standing in the room is projected onto the body of a patient laying on the support 10. The line lasers A and B each project one lateral line at a time onto the patient's body, line laser C projects a sagittal line and line laser D projects a line running transversely across the thorax. When the planes of the lateral lasers A and B coincide, all the light planes intersect in one point. However, the patient is normally aligned on a series of marks which result from the projection of the laser lines on the patient's body. For these marks, the patient is aligned on the movable patient support and thus he/she reaches an accurately specified position in relation to the therapeutic machine with its therapeutic beam.

Figure 2:
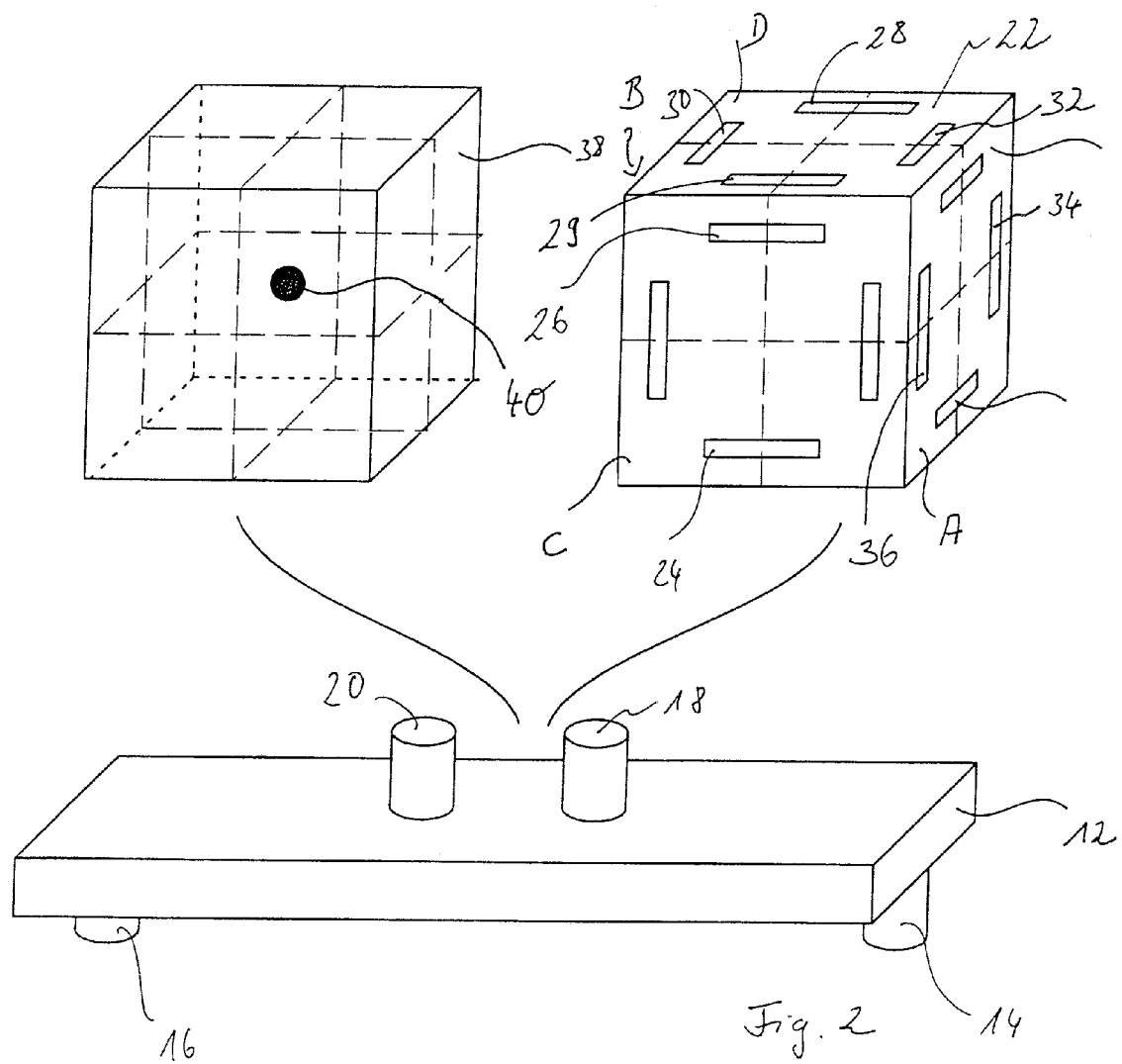
FIG. 2 shows the apparatus according to the present invention with a first and second measuring device.

FIG. 2 shows the apparatus according to the present invention with a carrier element 12. The carrier element 12 has two connection elements 14, 16 at one side, by which it can be arranged in a predefined position on the patient support. For this purpose, the patient support has recesses (so-called notches), which accommodate the pins 14, 16 and thus fix the position. On the opposing side of the carrier plate, two connection elements 18, 20 realised as pins are provided. The connection elements may have different diameters or a different cross section. Connection elements serve commonly to connect the carrier element with the patient support in a defined and reproducible manner. The connection elements are envisioned to be connected with two measuring devices 22, 38. The first measuring device 22 is designed as being substantially cube-like and has line sensors 24, 26 on at least three sides, which are arranged pair wise vertically with respect to each other. The sides of the measuring device 22 in FIG. 2 are designated corresponding to the lasers A to D from FIG. 1. On each of the sides, there are two pairs of line sensors at a time, so that even the laser light of two lasers can be acquired. Thus, for example, the line sensors 28 and 30 arranged on side D acquire the light of the laser C, whereas the line sensors 32 and 34 receive the light of the laser D. The line sensors on the first measuring device are able to detect the position in which the laser light hits the line sensor, and thus they permit to detect the position in space of the measuring device on the patient support.

Strictly speaking, no line sensors are necessary on side C, and on sides A and B only the line sensors 34, 36 for the lateral lasers A and B are necessary. However, the redundant measurement increases the accuracy.

The second measuring device 38 serves for detecting the position of the therapeutic beam. For detecting the beam position, a sample body 40 is arranged in the measuring device 38, which interacts with the beam. For instance, the sample body 40 may have a higher density than the remaining material of the measuring device, so that a shadow of the sample body 40 is formed on an imaging medium (not shown). Further, the recording medium is arranged such in the second measuring device 38 that the isocentre is represented on the same. Through this, by analysing the imaging medium it can be made sure that the distance between sample body 40 and isocentre is measured.

The measuring device 38 makes it possible to detect the position of the isocentre in relation to the sample body 40. The measuring device 22 permits to detect the point of intersection of the light planes spatially exactly. Thus, the position of the isocentre can be compared with the point of intersection of the lasers, and so an alignment of line laser and therapeutic beam in relation to each other can take place. For this purpose, the measuring devices 22 and 38 are set on the carrier plate 12 one after the other.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. An apparatus for checking the alignment of laser beams (A, B, C, D) for indicating a position in relation to a diagnostic and/or therapeutic machine, which has a isocentre, wherein the machine has a patient support (10) movable in its position, laser beams and isocentre being aligned in relation to each other such that the laser beams intersect with each other in the isocentre of the machine, wherein the machine has the following a carrier element (12), which is provided with means (14, 16) for being arranged in a predetermined position on the patient support (10) of the machine, a first and a second measuring device (22, 38), each one at a time being equipped with connection means for the carrier element (12), wherein the first measuring device (22) measures the position of the impingent laser beams with respect to a predetermined position in relation to the patient support (10), the second measuring device (38) records the position of the isocentre in relation to the predetermined position of the first measuring device.

2. An apparatus according to claim 1, characterised in that the first measuring device (22) has line sensors (24, 26, 30, 32, 34, 36), which acquire the position of the laser beams on the first measuring device.

3. An apparatus according to claim 1, characterised in that the first measuring device (22) has at least three line sensors, which are oriented by pairs in different directions in the space.

4. An apparatus according to claim 1, characterised in that the line sensors of the first measuring device are connected to an analysing unit, which determines whether the laser beams intersect with each other in the predetermined position with respect to the patient support.

5. An apparatus according to claim 4, characterised in that the analysing unit for adjusting the lasers into a predetermined position indicates which laser deviates into which direction from that position.

6. An apparatus according to claim 5, characterised in that the lasers are each one at a time equipped with means for moving their position, and the analysing unit generates control signals for aligning the lasers into a desired position.

7. An apparatus according to claim 1, characterised in that the second measuring device has a sample body and a holder for a recording material, which records an image of the sample body in the therapeutic beam.

8. An apparatus according to claim 7, characterised in that the sample body (40) is arranged in the second measuring device (38) in the predetermined position in relation to the patient support (10).

9. An apparatus according to claim 1, characterised in that the recording material in the second measuring device (38) is held such that an image of the sample body (40) and of the isocentre of the therapeutic beam is recorded.

10. An apparatus according to claim 1, characterised in that the predetermined position in relation to the patient support corresponds to the expected isocentre of the therapeutic machine.

11. A method for the alignment of laser beams for indicating a position in relation to a diagnostic and/or therapeutic machine, with the following steps a patient support is set into a defined reference position, a carrier element is arranged in a defined position on the patient support, using a first measuring device, a point of intersection of the laser beams is brought into coincidence with a predetermined position in relation to the patient support, using a second measuring device, the isocentre of the therapeutic beam is brought into coincidence with the predetermined position in relation to the patient support, wherein the first and the second measuring device are arranged on the carrier element and the position of the patient support in space, or of the carrier element in relation to the patient support, remains unchanged between the usage of the measuring device.

12. A method according to claim 11, characterised in that the second measuring device is used at first, and subsequently the lasers are aligned by using the first measuring device.

13. A method according to claim 11, characterised in that the first measuring device is used at first, and subsequently the therapeutic beam and/or the diagnostic beam are aligned using the second measuring device.

* * * * *